United States Patent [19]

Moormann

[11] Patent Number: 5,643,905
[45] Date of Patent: Jul. 1, 1997

[54] PHARMACEUTICAL FORMULATION FOR THE TREATMENT OF NICOTINE DEPENDENCE

[75] Inventor: Joachim Moormann, Werne, Germany

[73] Assignees: Therapie-System GmbH & Co., KG, Neuwied; Arzneimittelforschung GmbH & Co. KG, Werne, both of Germany

[21] Appl. No.: 495,608

[22] PCT Filed: Jan. 10, 1994

[86] PCT No.: PCT/EP94/00055

§ 371 Date: Oct. 30, 1995

§ 102(e) Date: Oct. 30, 1995

[87] PCT Pub. No.: WO94/16708

PCT Pub. Date: Aug. 4, 1994

[30] Foreign Application Priority Data

Jan. 23, 1993 [DE] Germany ............ 43 01 782.7

[51] Int. Cl.$^6$ ................................ A61K 31/55
[52] U.S. Cl. ......................... 514/215; 514/813
[58] Field of Search ........................... 514/215, 813

[56] References Cited

U.S. PATENT DOCUMENTS

| | | | |
|---|---|---|---|
| 3,742,951 | 7/1973 | Zaffaroni | 128/268 |
| 3,760,805 | 9/1973 | Higuchi | 128/260 |
| 3,797,494 | 3/1974 | Zaffaroni | 128/268 |
| 3,987,790 | 10/1976 | Eckenhoff et al. | 128/160 |
| 3,996,934 | 12/1976 | Zaffaroni | 128/268 |
| 4,031,894 | 6/1977 | Urquhart et al. | 128/268 |
| 4,137,300 | 1/1979 | Sheth et al. | 424/21 |
| 4,597,961 | 7/1986 | Etscorn | 424/28 |
| 4,769,028 | 9/1988 | Hoffmann et al. | 424/443 |
| 5,089,267 | 2/1992 | Hille et al. | 424/449 |
| 5,519,017 | 5/1996 | Opitz | 514/215 |

FOREIGN PATENT DOCUMENTS

| | | |
|---|---|---|
| 3 315 272 | 3/1986 | Germany . |
| 3 629 304 | 3/1988 | Germany . |
| 3 843 239 | 2/1990 | Germany . |
| 4 010 079 | 7/1992 | Germany . |

*Primary Examiner*—Raymond Henley, III
*Attorney, Agent, or Firm*—Wenderoth, Lind & Ponack

[57] ABSTRACT

The present invention relates to the use of galanthamine and the pharmaceutically acceptable acid addition salts thereof for the treatment of nicotine dependence. The active substances are released from pharmaceutical formulations, e.g., orally, transdermally, or otherwise parenterally in a continuous and controlled manner.

7 Claims, No Drawings

PHARMACEUTICAL FORMULATION FOR THE TREATMENT OF NICOTINE DEPENDENCE

This application is a 371 of PCT/EP94/00055 filed Jan. 10, 1994.

DESCRIPTION

The present invention relates to pharmaceutical formulations for the treatment of nicotine dependence.

The present invention is particularly directed to pharmaceutical formulations and devices by which galanthamine or one of its pharmaceutically acceptable acid addition salts is released in a controlled, for instance continuous manner to treat nicotine dependence.

The dependence on nicotine complies with all criteria of drug addiction defined by the WHO:
compulsive use
psycho-active effects
influence on the behavior
stereotyped consumption habits
abstinence symptoms on withdrawal or tolerance development Accordingly, smoking is not a "bad habit" and cannot be suppressed by will alone in all cases. Pharmacologists discovered nicotine receptors in the brain which are the biological explanation for the fact that so many smokers, despite their high motivation and good psychological support, backslide again and again.

In 1975, this finding resulted in a completely new therapeutic approach, the nicotine supply via chewing gum. Although welcomed enthusiastically at first, the system soon showed drawbacks. The bitter taste and the poor social acceptance of the chewing gums were some of the objections. In addition, abuse by overdosage also occured with these systems.

All these drawbacks led to the development of transdermal therapeutic systems which comprise nicotine, e.g., described in German patent DE 36 29 304 and U.S. Pat. No. 4,597,961.

When nicotine is administered transdermally, taste is of no importance, the application is invisible, the substance is delivered without oral substitutive gratification, and plasma peaks are avoided.

Observed side effects are skin irritations at the site of application, i.e. reddenings, slight swellings and itching, which in some cases caused the stop of the therapy.

In addition, another disadvantage of this nicotine therapy is the fact that this form of treatment does not take into account the extreme toxicity of nicotine.

Accordingly, there is a demand for drugs which reliably suppress the symptoms of nicotine dependence; however, the therapeutic doses of the active substance may not have a toxicity comparable to that of nicotine.

Until today, substances from the following groups have been used to treat nicotine dependence:
natural substances without nitrogen, e.g. δ-pyrones, citric acid, acetic acid, camphor, glucose, vitamins, terpenes, and others
alkaloids, e.g. lobeline, caffeine and apocynaceae alkaloids
tricyclic antidepressants, e.g. fluoxetin
clonidine
pyrrolopyrimidine The diversity of therapy principles alone reveals that an efficacious drug for the treatment of nicotine dependence which is not as toxic as nicotine has not yet been found.

Accordingly, it is the object of the present invention to provide a drug in an oral, transdermal, or otherwise parenteral formulation which allows a controlled release of the drug to the greatest possible extent and ensures a reduction in the desire for nicotine. The term parenteral is used to include all forms of application, except for the oral form, such as the rectal, intravenous, intramuscular, intraperitoneal and nasal form of administration.

According to the present invention this object is surprisingly achieved by a formulation for the treatment of nicotine dependence, which is characterized in that it comprises an effective amount of the active substance galanthamine (4a, 5,9,11,12-hexahydro-3-methoxy-11-methyl-6H-benzofuro [3a, 3, 2-ef] [2] benzazepine-6-ol) or one of the pharmaceutically acceptable acid addition salts thereof.

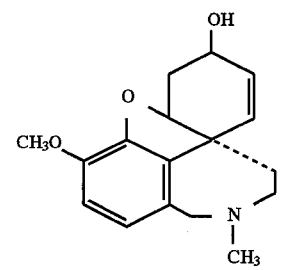

This solution is surprising all the more since, although galanthamine has been examined in great detail and the pharmacological effects thereof have been studied thoroughly, the application of a galanthamine-containing formulation to treat nicotine dependence according to the present invention has not been described until today.

Owing to its pharmacological properties galanthamine belongs to the group of reversibly acting cholinesterase inhibitors, its effects are similar to those of physostigmine and neostigmine, however, it stands out for particular specific properties. The therapeutic range of galanthamine is three to six times broader since it is not as toxic as physostigmine or neostigmine.

This advantage compensates for its slightly lower cholinesterase inhibiting-action, relative to the unit of weight.

In medicine, galanthamine is used for various indications, e.g. in anaesthesia to compensate muscle relaxation after administration of non-depolarizing muscle relaxants. The extensive duration of action makes galanthamine which combines the properties of physostigmine and neostigmine, a valuable drug in anaesthesiology, since many patients suffer from a central anticholinergic syndrome after a general anaesthesia. In addition, it is a useful antidote for neuroleptanalgesia.

In contrast to neostigmine, galanthamine passes the blood-brain-barrier and antagonizes the cerebral effects of anticholinergic poisons. Galanthamine promotes awakening from the twilight sleep caused by scopolamine.

In neurology, galanthamine is used to treat facial nerve pareses and other mono and polyneurophaties, residual paraplegia after polymyelitis or brain and spinal cord injuries, and in myasthenia gravis. In ophthalmology, galanthamine is used for the symptomatic treatment of the narrow-angle glaucoma. The use of galanthamine in the treatment of the Alzheimer's disease is in an experimental stage.

In addition, it was proposed to use galanthamine in clinical studies on alcohol withdrawal (Opitz, K., DE-PS 40 10 079).

Galanthamine is obtained, for example, by isolation from the caucasian snowdrops Galanthus woronowi Vel., Amaryllidaceae, or by synthesis.

Drug forms releasing active substances in a controlled manner are known in the state of the art. The administration of pharmaceutically effective compounds by means of such formulations may be effected via the oral, transdermal or otherwise parenteral route. In such drugs galanthamine may be present as such or in the form of pharmaceutically acceptable acid addition salts, e.g. as hydro halide, in particular hydrochloride or hydrobromide, or as a salt of another pharmaceutically acceptable acid. Usually, these means additionally comprise adjuvants, such as carriers, free-flow agents, solvents and oils, the kind and amount of which may vary with the respective form of administration. In general, the content of active substance in the drug ranges between 0.1 and 50%-wt., preferably between 2 and 15%-wt., calculated as free galanthamine.

Some suitable oral formulations for oral administration that are within the scope of the present invention will be described in the following.

For example, in such a formulation the pharmaceutical active substance is encapsulated in a semipermeable membrane, e.g. in cellulose acetate. A tiny hole is bored into the capsular material by means of a piercer or laser. Within the body of the treated patient water is absorbed through the capsular material. The pharmaceutical active substance is forced through the tiny aperture in the desired gradual, constant and controlled manner by osmotic pressure. Such systems are described, e.g., in U.S. Pat. Nos. 3,760,805 and 3,987,790. The pharmaceutical active substances may be present in the systems in solid form or absorbed to ion-exchange resins.

Another system for oral administration is described by Sheth and Leeson in U.S. Pat. No. 4,137,300. This patent describes a formulation comprising a wax matrix.

The active substances of the present invention are administered by means of adequate formulations in a convenient and suitable manner. The solid active substances may be administered in solution or as suspension. The solution or suspension medium may be an aqueous or organic one. Suitable solution or suspension media for galanthamine include, for example, water, silicone fluid or mineral oil.

In order to facilitate the administration of a compound by means of a formulation as described above, a free-flow agent may be added to the system. Some suitable free-flow agents for oral formulations, for example, include polyethylene glycol, hydroxypropyl methyl cellulose and sugar.

In a formulation for the transdermal administration of compounds according to the present invention, the pharmaceutical active substance may be comprised in a matrix from which it is released in the desired gradual, constant and controlled manner. The permeability of the matrix during the release of the compound is based on diffusion. Such a system is described in German patent 33 15 272 (U.S. Pat. No. 4,769,028). This system consists of an impermeable cover layer, an oversaturated active substance reservoir of a polymeric matrix, which is attached to the cover layer and has a particular construction, a pressure sensitive adhesive layer bonded to the reservoir and permeable to the active substance, and a removable protective layer which covers the pressure sensitive adhesive layer and is removed prior to use. Systems having a reservoir layer whose self-tackiness is strong enough to form the pressure sensitive adhesive layer are also suitable.

German patent DE 38 43 239 (U.S. Pat. No. 5,089,267) describes such a system.

When the active substance is absorbed through the skin the person to be treated thus receives a controlled and predetermined active substance flow.

Other suitable transdermal formulations are described in U.S. Pat. Nos. 3,742,951; 3,797,494; 3,996,934, and 4,031,894. In principle these formulations consist of a backing layer representing one surface, an adhesive layer permeable to the active substance and representing the other surface, and, finally, a reservoir comprising the active substance between the two layers forming the surfaces. Alternatively, the active substance may be comprised within a variety of microcapsules which are distributed in the permeable adhesive layer. In any case, the active substance is continuously released from the reservoir or the microcapsules through a membrane into the adhesive layer which is permeable to the active substance and in contact with the skin or mucosa of the treated person. In the case of microcapsules the capsular material may act as membrane too.

Suitable formulations to apply galanthamine and the salts thereof in another parenteral manner are those allowing a depot effect of the active substance. In this case, the formulation is applied as injectable solution on a non-aqueous base. Suitable solvents are known to those skilled in the art. Vegetable oils specified by some pharmacopoeias are mentioned as example, they include peanut oil, olive oil, almond oil, sunflower oil, soybean oil, and sesame oil. Caster oil often has a particularly favorable solubility for drugs; in addition, oils of animal origin are also suitable.

The oils are physiologically indifferent and well tolerated. A precondition for this is that they are specially purified and have low acid and peroxide values. Since an intravenous application is not possible due to the nonexistent miscibility within the blood serum and because it may result in pulmonary embolism, they may only be used for intramuscular and subcutaneous injection preparations. Oily solutions and suspensions remain at the site of application for a rather long period (frequently up to one month) and release the active substances in a protracted manner.

The dosage of galanthamine or its pharmaceutically acceptable acid addition salts must be large enough and must be effected over a long period to achieve a lasting effect, and it requires individual stabilization/control.

The present invention will be illustrated by the following example.

Example:

The influence of galanthamine on the smoking of healthy test persons

During a test series for a transdermal therapeutic system, which in vivo releases about 10 mg galanthamine base per day, two smokers were also among the test persons since "smoking" was no criterion to exclude them from the test. Most surprisingly, both smokers showed a noticeable suppression in the desire for cigarettes. The duration of application amounted to 24 hours. The data is listed in the following table:

TABLE 1

|  | Cigarette consumption without galanthamine | Cigarette consumption after transdermal administration of 10 mg/day galanthamine |
|---|---|---|
| Male test person | 15–20 cigarettes/day | none |
| Female test person | an average of 60 cigarettes/day | 7 cigarettes/day |

Table 1 shows that the single administration of 10 mg galanthamine/day resulted in a considerable reduction in the cigarette consumption.

I claim:

1. A method for the treatment of nicotine dependence which comprises administering to a patient suffering from such dependence an effective amount of galanthamine or a pharmaceutically acceptable acid addition salt thereof.

2. A method according to claim 1 wherein the administration is orally.

3. A method according to claim 1 wherein the administration is parenterally.

4. A method according to claim 1 wherein the administration is transdermally.

5. A method according to claim 1 wherein the galanthamine or salt thereof is administered in a composition comprising the galanthamine or salt thereof in an amount of 0.1 to 50% by weight calculated as free galanthamine.

6. A method according to claim 5 wherein the amount is 2 to 15% by weight.

7. A method according to claim 5 wherein the composition also contains at least one suitable adjuvant.

* * * * *